United States Patent
Buttle

(10) Patent No.: US 6,854,336 B2
(45) Date of Patent: Feb. 15, 2005

(54) MEASUREMENT OF STRESS IN A FERROMAGNETIC MATERIAL

(75) Inventor: David John Buttle, Wantage (GB)

(73) Assignee: AEA Technologoy PLC, Didcot (GB)

( * ) Notice: Subject to any disclaimer, the term of this patent is extended or adjusted under 35 U.S.C. 154(b) by 0 days.

(21) Appl. No.: 10/433,830

(22) PCT Filed: Dec. 18, 2001

(86) PCT No.: PCT/GB01/05600

§ 371 (c)(1), (2), (4) Date: Jun. 9, 2003

(87) PCT Pub. No.: WO02/50503

PCT Pub. Date: Jun. 27, 2002

(65) Prior Publication Data

US 2004/0040389 A1 Mar. 4, 2004

(30) Foreign Application Priority Data

Dec. 20, 2000 (GB) .......................................... 0031216.5

(51) Int. Cl.$^7$ ................................................. G01B 7/16
(52) U.S. Cl. ....................................................... 73/779
(58) Field of Search ........................ 73/772, 773, 779, 73/794, 801, 862.69

(56) References Cited

U.S. PATENT DOCUMENTS

| | | | | |
|---|---|---|---|---|
| 4,117,402 A | * | 9/1978 | Zangger et al. | 324/220 |
| 4,301,677 A | * | 11/1981 | Fisher | 73/105 |
| 4,399,692 A | * | 8/1983 | Hulsing et al. | 73/152.54 |
| 4,452,087 A | * | 6/1984 | D'Antonio | 73/786 |
| 4,491,022 A | * | 1/1985 | de la Cruz | 73/783 |
| 5,942,750 A | * | 8/1999 | Sannerhaugen et al. | 250/227.14 |

FOREIGN PATENT DOCUMENTS

JP           8122170           5/1996

OTHER PUBLICATIONS

English language abstract of JP 8122170.

* cited by examiner

*Primary Examiner*—Max Noori
(74) *Attorney, Agent, or Firm*—William H. Holt

(57) ABSTRACT

Stress in the wall of a pipe (12) is measured using a pig (10) carrying at least one linear array of probes, so that the probes (30) in the array pass in succession over a location on the pipe wall. Each probe (30) comprises an electromagnetic core (32) with two spaced apart electromagnetic poles (34), and a magnetic sensor (36) arranged to sense the reluctance of that part of the magnetic circuit between the poles (34), and an alternating magnetic field is generated in the electromagnet means and consequently in the pipe wall. Successive probes (30) in the array are oriented differently so that the corresponding orientations of the magnetic field in the pipe wall are different. Preferably the probes (30) also include sensors (38) between the two poles (34) to sense magnetic flux perpendicular to the direction of the free space magnetic field between the poles. The signal from the sensor (36) and (38) enable the stress to be determined. Such an array may be used with any long object of ferromagnetic material.

8 Claims, 3 Drawing Sheets

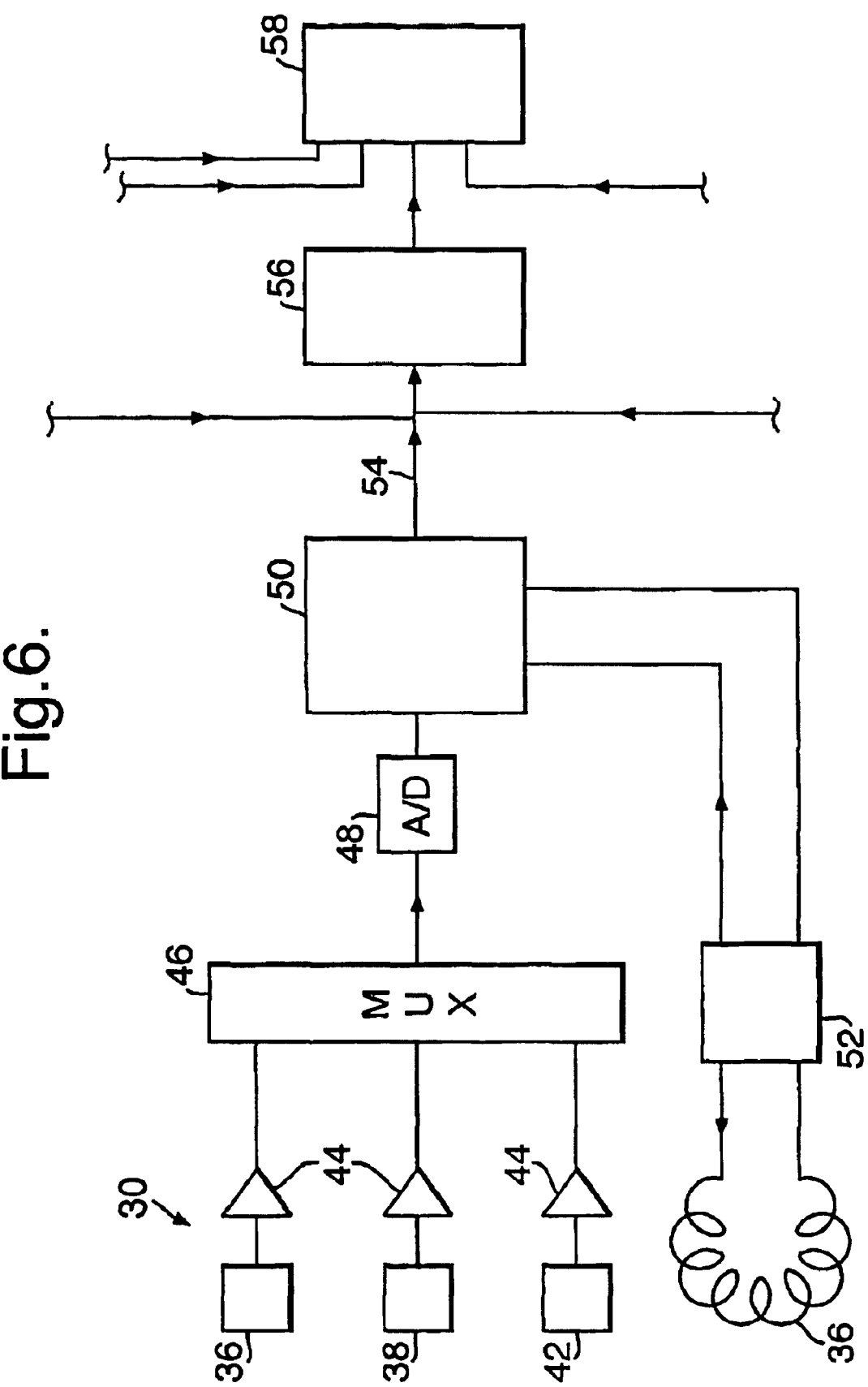

MEASUREMENT OF STRESS IN A FERROMAGNETIC MATERIAL

This invention relates to a method and apparatus for measuring stress in a ferromagnetic material, in particular in long objects. It is for example suitable for measuring stresses in steel pipelines such as those used to carry oil or gas.

The stresses in pipelines arise from various causes including changes of temperature, movement of and pressure from the surrounding soil, and the pressure of the fluid contained within the pipeline. There may also be residual stresses arising from the fabrication of the lengths of pipe, the welding of the lengths together, and any bending that the pipe lengths are subjected to during construction. The residual stresses arising from fabrication will depend upon the way in which the pipe lengths are made, and if they have been given a stress-relieving heat treatment. In any event the principal stress directions are usually in the circumferential and longitudinal directions. A variety of magnetic techniques are known to have some sensitivity to stress, although magnetic measurements are usually also affected by other material properties such as microstructure. A way of measuring stress in a steel plate is described in GB 2 278 450, this method using a probe containing an electromagnetic core to generate an alternating magnetic field in the plate, and then combining measurements from two sensors, one being a measure of stress-induced magnetic anisotropy, and the other being a measure of directional effective permeability. The probe is gradually turned around so the magnetic field has a plurality of different orientations in the plate, and these measurements are taken at each such orientation. To achieve good spatial resolution, and to minimize the effects of curvature of the surface, the use of a small probe is recommended, less than 50 mm in diameter and preferably less than 20 mm. This procedure enables the stress to be accurately measured at a specific location in a steel plate. However, for measuring stresses in a long object it would be desirable to be able to make measurements while moving along the length of the object.

An apparatus for measuring stress in an object of ferromagnetic material, the apparatus comprising a linear array of probes, and a support structure for the array that is arranged to move relative to the object so that the probes in the array pass in succession over a location on the surface of the object; each probe comprising an electromagnet means defining an electromagnetic core and two spaced apart electromagnetic poles, and means to supply an alternating electric current to generate an alternating magnetic field in the electromagnet means and consequently in the object, and a magnetic sensor arranged to sense the reluctance of that part of the magnetic circuit between the poles of the electromagnet means and to generate a corresponding signal that can be resolved into components in phase with the alternating current and in quadrature to it; wherein the frequency of the alternating magnetic field, the width of each probe, and the velocity of the array relative to the object are such that the said frequency is significantly greater than that calculated by dividing the said velocity by twice the said width; and wherein successive probes in the array are oriented differently so that the corresponding orientations of the magnetic field in the object are different.

Preferably the array comprises a linear array of probes wherein at least some of the probes include a first magnetic sensor between the two poles and arranged to sense magnetic flux density perpendicular to the direction of the free space magnetic field between the poles, and at least some of the probes include a second magnetic sensor arranged to sense the reluctance of that part of the magnetic circuit between the poles of the electromagnet means.

The first sensor would detect no signal if the material were a flat plate and exactly isotropic; however stress induces anisotropy into the magnetic properties of the material, and so the signals received by the first sensor are a measure of this stress-induced magnetic anisotropy (SMA). The variations in the SMA signals from probes of different orientations, as they pass over a location on the object, enable the directions of the principal stress axes to be accurately determined. The SMA signals can also be related to the stress.

The second sensor provides a measure of the permeability of the material through which the flux passes between the poles, and so provides a signal indicative of the effective permeability of the material; the corresponding measurements from probes of different orientations, as they pass over a location on the object, hence indicate the effective permeability in different directions, which is referred to as directional effective permeability (DEP). The DEP signals enable the value of stress to be determined.

The DEP signal from a probe is preferably backed-off, i.e. processed by first subtracting a signal equal to the signal from that-sensor with the probe adjacent to a stress-free location. The small changes in DEP due to stress are then easier to detect. The DEP signals can then be resolved as a component in phase with the current creating the alternating field, and a component in quadrature to that (analogous to resistance and reactance in the impedance plane). If the gap between the surface and the probe (the lift-off) varies, this also has an effect on the DEP signals. This change corresponds to a direction in the impedance plane oriented in a direction referred to as the lift-off direction. Hence to avoid spurious effects due to changes in lift-off, the output DEP signal is that component of the signal which, in the impedance plane, is perpendicular to the lift-off direction. The values of this resolved component obtained from different probes enable you to determine the values of the resolved component with the magnetic field aligned with the directions of the principal stress axes, and hence to calculate the values of the principal stresses at that location. Preferably the DEP signals from the probes are digitized initially, and the backing-off and lift-off corrections are applied in the analysis of the digital signals.

Alternatively, if it is only desired to determine the bending stress in a pipeline, the DEP measurements obtained on diametrically opposite sides of the pipe might merely be subtracted from each other.

Several of these concepts are analogous to those used in GB 2 278 450 mentioned above, except that there is an array of probes, and that the array moves relative to the surface. The magnetic fields will tend to be distorted by the movement of the array, which generates eddy currents. To achieve penetration into the surface of the ferromagnetic object it is desirable to operate at alternating frequencies less than 200 Hz, more preferably between 10 Hz and 100 Hz, and it will be appreciated that at such low frequencies there will be a significant movement of the probe during a single period of the alternating field. Furthermore when scanning at linear speeds up to a few metres per second it is difficult to avoid there being variations in lift-off of the order of say 1 mm or so, and it would be desirable if the measurement technique could be substantially unaffected by such variations.

It is therefore desirable to have each probe being of width and breadth at least 75 mm, more preferably at least 100 mm, though preferably no larger than 350 mm. Such large probes are less sensitive to lift-off, and higher speeds of travel are attainable before eddy currents pose a problem. Preferably each probe also incorporates a proximity sensor to provide a signal indicating the lift-off for that probe, the signals from the proximity sensor being calibrated to indicate the corresponding degree of attenuation of the DEP and SMA signals at each value of lift-off, so that the DEP and SMA signals can be corrected.

Generally, the more different probe orientations are used for taking measurements the more accurate the determination of stress levels and principal axes can be. In many cases the principal stress axes can be assumed to be aligned in particular directions—axial and circumferential directions in the case of a pipe, for example—so that the signal maxima and minima for DEP would be expected to be along these directions, and those for SMA would be along the bisection angles between these directions. In the method of GB 2 278 450, measurements were described as being taken at 10° intervals, but in contrast the array of the present invention might have fewer than ten probes, for example it might have four probes oriented at 0°, 45°, 90° and 135° relative to the direction of motion.

The invention will now be further and more particularly described, by way of example only, and with reference to the accompanying drawings, in which:

FIG. 6 shows, as a block diagram, the electronic circuitry of the pig of FIG. 1.

Figure 1:
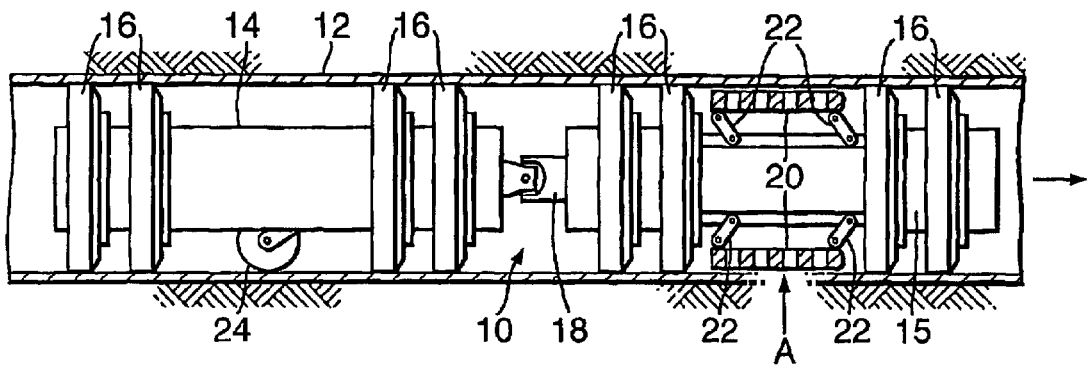
FIG. 1 shows an overall view, partly in section, of a pipeline inspection pig incorporating arrays of probes of the invention.

Referring now to FIG. 1, an inspection pig 10 is shown for measuring stresses in the wall of an underground pipe 12. The pig 10 consists of two generally cylindrical housings 14 and 15 each of which is supported within the pipe 12 by four resilient cup seals 16 oriented so the pig 10 can move from left to right (as shown) along with the flow of the fluid in the pipe 12, the two housings 14 and 15 being linked together by a universal coupling 18. The housings 14 and 15 contain a battery to provide a power supply, signal processing units and data recording units (not shown), whose operation is described later. The front housing 15 carries four linear arrays of probes (only two are shown; the probes themselves are not shown in FIG. 1) each array being carried by a support bar 20 connected by resiliently mounted arms 22 so the array is urged outwardly against the inner surface of the wall of the pipe 12; each array is aligned parallel with the longitudinal axis of the pipe 12, and the arrays are equally spaced around the axis so they are, for example, above, below, and on each side of the housing 15. The rear housing 14 carries a wheel 24 that is arranged to roll along the inner surface of the pipe 12, enabling the distance travelled by the pig, and its speed, to be determined.

Figure 2:
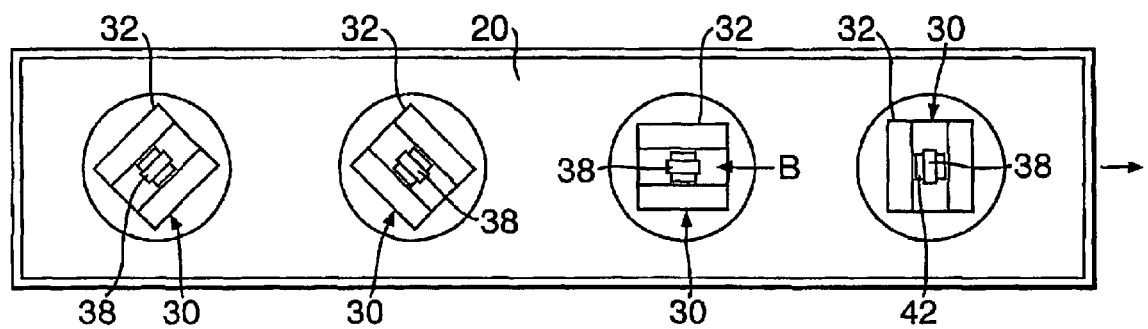
FIG. 2 shows a plan view, in the direction of arrow A of FIG. 1, of an array of probes.
Figure 3:
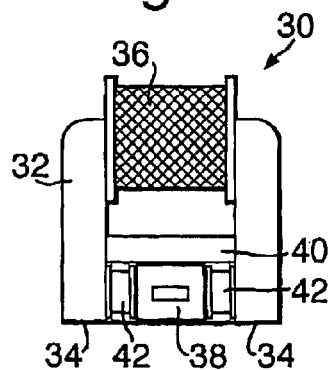
FIG. 3 shows an elevation, in the direction of arrow B of FIG. 2, of one of the probes.

Referring now to FIG. 2, the support bar 20 carries four probes 30. Referring also to FIG. 3, each probe 30 includes a U-core 32 of silicon iron which defines two rectangular poles 34 in a common plane, each pole being 110 mm by 30 mm, and the space between the poles being 110 mm by 50 mm. The faces of the poles 34 are slightly curved to match the curvature of the wall of the pipe 12. The separation between successive probes 30 is also 110 mm. Around the upper end of the U-core 32 is a former on which are wound two superimposed coils 36. One coil 36 has 500 turns, and in use is supplied with an AC current of 0.2 A, at a frequency of 60 Hz; this is the energising coil 36. When energised, this generates an alternating magnetic field in the U-core 32 and in the adjacent wall of the pipe 12, this magnetic field being small compared to the saturation field for the material of the pipe wall. The other coil 36 is a sensing coil which provides DEP signals.

Midway between the two poles 34 is a former on which is wound a 1,000-turn rectangular coil 38, each turn lying in a plane parallel to that of FIG. 3, so that the longitudinal axis of the coil 38 is perpendicular to the line between the centres of the poles 34 (i.e. perpendicular to the free-space magnetic field direction, that is the direction of the magnetic field when there is no pipe 12 present). The coil 38 is supported on a support plate 40 fixed between the arms of the U-core 32 so the lower face of the coil 38 is in the plane of the poles 34. The coil 38 provides the SMA signals. Between the sides of the coil 38 and the sides of the poles 34 are two halves of a proximity-sensing coil 42 whose longitudinal axis is parallel to the free-space magnetic field direction (the two halves being electrically in series). This coil 42 detects leakage flux, and is significantly affected by lift-off. Both the DEP and SMA signals are amplified by a head amplifier before further processing.

Referring again to FIG. 2, the four probes 30 are of identical structure but are oriented differently: working from the right (as shown) that is to say from the front of the support bar 20, the first probe is oriented with the magnetic field parallel to the direction of motion; the second probe is oriented with the magnetic field at 90° to the direction of motion; the third probe is oriented with the magnetic field at 45° to the direction of motion; and the fourth probe is oriented with the magnetic field at 135° to the direction of motion.

Thus in operation as the energising coils 36 are energized the wall of the pipe 12 adjacent to each probe 30 experiences alternating magnetic fields. The magnetic field penetrates only a limited distance into the steel, essentially because of the skin effect which for a standard mild steel indicates a penetration depth of about 17 mm per reciprocal root Hz, which for 20 Hz indicates a penetration of about 3.8 mm and for 60 Hz a penetration of about 2.2 mm. If a tensile stress exists in the pipe wall and the applied magnetic flux is at an angle with respect to the stress direction, the field will tend to rotate towards the tensile axis. This affects both the SMA and DEP signals, and in particular the largest SMA signal occurs when the probe direction approximately bisects the principal axes for the stress. In the context of the pipe 12 the principal stress directions can be expected to be circumferential (hoop) and longitudinal, so that the third and fourth probes 30 can be expected to give the largest SMA signals.

Figure 4:
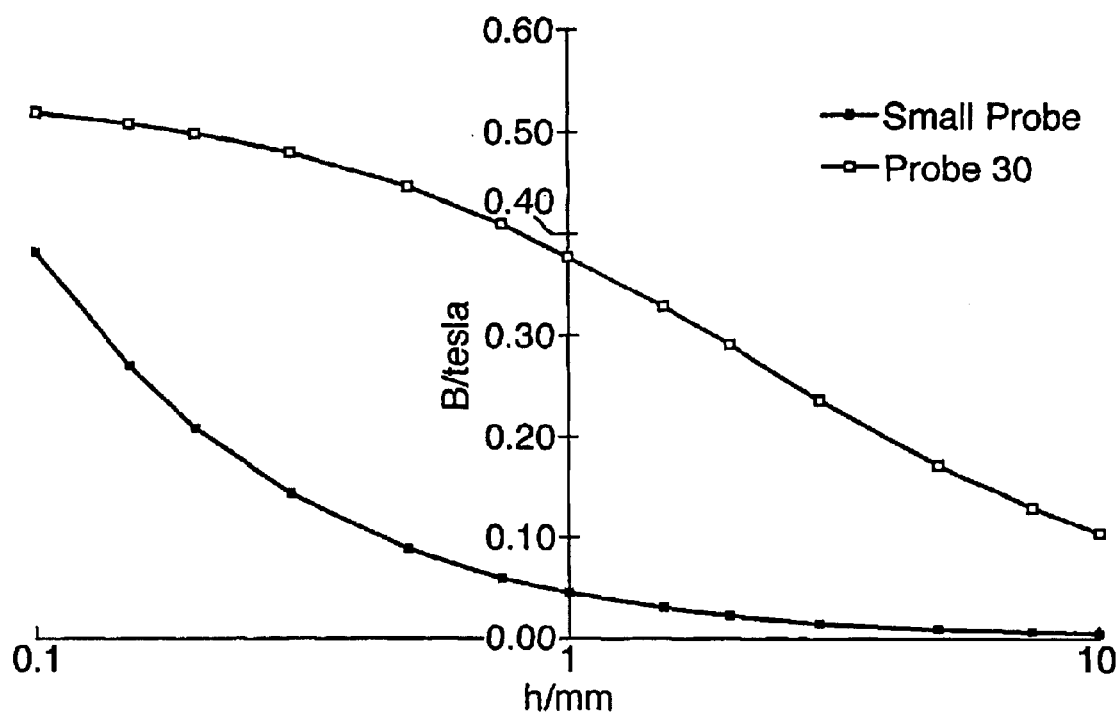
FIG. 4 shows graphically the variation of magnetic field in the wall of the pipe as the separation between a probe and the wall varies.

Lift-off does affect the magnitude of the signals, but the sensitivity to lift-off is much less than for a smaller probe. Referring to FIG. 4 this shows graphically the variation in the magnetic flux density, B, in the pipe wall adjacent to the probe 30 for different values of lift-off, h, and for comparison the corresponding values with a small probe that is 12 mm by. 12 mm (substantially as described in GB 2 278 450 B). The decrease in flux density, which is indicative of the decrease of the DEP and SMA signals, is much less for the larger probe 30.

The size of the probe 30 also has an influence on its sensitivity to stress. Assuming that a change of stress results in a change of permeability of the pipe wall of 10%, the overall change of reluctance in the magnetic circuit (which corresponds to the DEP measurement) has been calculated as 3.44% for the probe 30, compared to only 0.79% for the small probe.

Typically the pig 10 might move along the pipe 12 at a speed between 1 and 4 m/s, e.g. 2.4 m/s. The movement of the probes 30 relative to pipe wall will also affect or distort the magnetic field in the wall. This effect can be described in terms of eddy currents. Considering the first probe 30, for which the magnetic field is parallel to the direction of motion, the predominant frequency f of the induced eddy currents is determined by the distance d between the centres of the poles 34 and the velocity v. It arises when the velocity is just sufficient to move the probe 30 twice the distance required for the magnetic north pole to be where the south pole was one cycle previously. That is to say:

$$f=v/2d,$$

and the predominant frequency will be similar for the other probes 30. The desired signals, in this example, are generated at a frequency of 60 Hz, so the eddy currents signals are preferably significantly less than this frequency. Hence the frequency of the generated alternating magnetic field should be significantly greater than the frequency calculated by dividing the velocity of the array relative to the surface by twice the width of a probe 30. For example if the signals are processed using a filter of bandwidth 40 Hz, then the eddy current frequency, f, is preferably less than 20 Hz; more generally, the eddy current frequency, f, should differ from the drive frequency by at least the bandwidth of the filter. The probe 30 has a value of d about 80 mm, so at a velocity of 2.4 m/s the expected eddy current frequency, f, would be 15 Hz, which would be sufficiently low. It will be appreciated that if the pig 10 was required to move at much higher velocities then this eddy current distortion could be eliminated by using even larger probes, although this would clearly reduce the resolution of the measurements.

Figure 5:
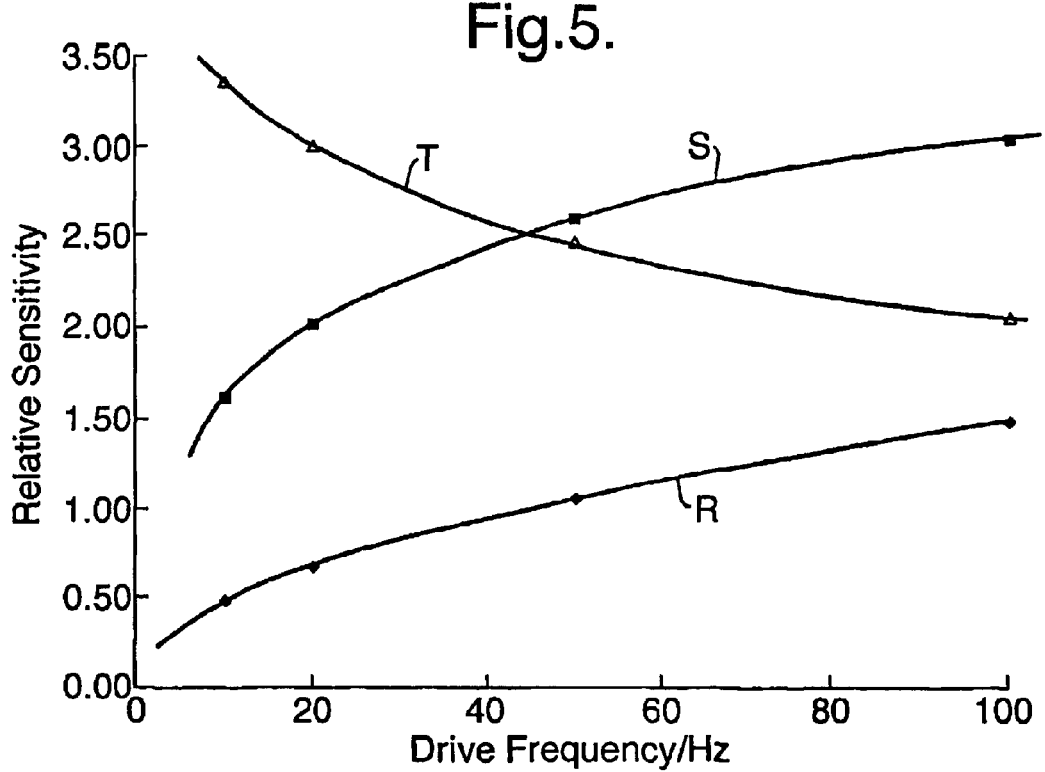
FIG. 5 shows graphically the variations of the relative sensitivity of a probe to stress and to lift-off, as the drive frequency varies.

The selection of the drive frequency also influences the sensitivity of the probe 30 to both stress and lift-off. In practice the lift-off may be expected to lie in the range 1 to 5 mm as the pig 10 moves along the pipe 12 and the probes 30 may be provided with wear-resistant non-magnetic spacers (not shown), for example of ceramic, to ensure the coils 38 and 42 are not damaged by contact with the pipe 12. As the drive frequency increases, the skin depth within the pipe wall decreases as mentioned earlier, so that the reluctance of the part of the magnetic circuit in the pipe wall increases, and consequently any changes due to stress have a larger effect on the DEP signal. Equally, at a higher frequency the gaps between the poles 34 and the pipe wall contribute a smaller proportion of the reluctance in the magnetic circuit, so the probe 30 becomes less sensitive to lift-off. This is illustrated in FIG. 5, to which reference is now made. This shows the relative sensitivity to stress (graph S), the relative sensitivity to lift-off (graph T) and the ratio of stress sensitivity to lift-off sensitivity (graph R). This would suggest that higher frequencies are beneficial, although at higher frequencies the power consumption is greater; unless the pig 10 also contains a dynamo (which might be linked to the wheel 24), then higher power consumption will decrease the running time, which is determined by the capacity of the battery.

The interpretation of the SMA and DEP signals can be performed in a similar way to that described in GB 2 278 450. The stress state in the pipe surface can be characterized by three parameters: the two principal., stress levels, and the principal stress direction (the other principal stress direction being orthogonal). In the case of the pipe 12 it is reasonable to assume that the principal axes are longitudinal and circumferential. Hence in the case of the DEP signals the most significant values are those obtained with the first and second probes 30 (i.e. at 0 and 90°), while the most significant SMA values are those obtained with the third and fourth probes 30 (i.e. at 45 and 135°). In practice, the DEP signals vary as a cosine graph with angle, so that measurements along other orientations improve the assessment of the maximum and minimum values.

Before measurements are made, the array of probes 30 is placed in a region of a pipeline where the stress is negligible (or at any rate known), and the values of the DEP signals are backed off to give zero signal. The small changes in DEP due to stress are then easier to measure. The probes 30 are then gradually moved away from the pipe surface, and the signals from the proximity coil 42 are noted at different values of lift-off, as are the values of attenuation of the DEP and SMA signals. The signals from the proximity coil 42, the SMA signals from the coil 38 and the DEP signals from the sensing coil 36 can each be resolved as a component in phase with the current creating the alternating field, and a component in quadrature to that; these components correspond to resistance and reactance in the impedance plane. To avoid spurious effects due to changes in lift-off, the output DEP signal is that resolved in a direction at right angles to the effect of lift-off in the impedance plane. The signals from the proximity coil 42 are resolved in a direction at right angles to the effect of stress in the impedance plane, so that the resultant proximity signal depends only on lift-off. Both the back-off and the lift-off initialisation for the DEP measurements, and the resolution and calibration for the proximity coil 42 must be performed before measurements can be made.

During use of the pig 10 the signals from the proximity coils 42, the DEP sensing coil 36 and the SMA coil 38 are amplified and stored. Some signal processing may however be performed in the pig 10 before the data is stored. The stored data is subsequently downloaded and analyzed to determine the stresses along the pipe 12. In particular the signals are preferably backed off (in the case of the DEP signals), demodulated into in-phase and quadrature components, and passed to a low pass filter output (for example with a cut-off at 40 Hz) to determine the DC values, and (in the case of the DEP signal's) resolved in the direction perpendicular to the effect of lift off. This signal processing may be performed before storage. The signals from the proximity coil 42 (resolved perpendicular to the effect of stress) can be used to determine the appropriate amplification of the DEP and SMA signals to compensate for their attenuation due to lift-off. The appropriately resolved signal values for DEP and SMA can then be amplified by the appropriate amounts. All these signal processing steps are preferably performed digitally.

Referring to FIG. 6, the electronic system within the pig 10 is shown diagrammatically. Within each probe 30 each sensor coil, i.e. the DEP coil 36, the SMA coil 38 and the proximity coil 42, is provided with a pre-amplifier 44 to buffer the impedance of the coil from the electrical connection to the remaining parts of the electronics, and to amplify the signal sufficiently to make it robust against electrical noise in the environment. The amplified signals are supplied via a multiplexer 46 and an analog to digital converter 48 to a digital signal processor 50. Each probe 30 also has a drive circuit 52 to provide the 60 Hz drive current to the energising coil 36, and the drive circuit 52 also supplies a signal of the same phase to the signal processor 50. The signal processor 50 de-modulates and filters the individual sensor outputs as described above, and stores the data temporarily. The data is then provided via a serial communication bus 54 and a node processor 56 to a data storage unit 58.

The corresponding signals from other probes 30 in an array are also supplied via the serial bus 54 to the processor 56. The data storage unit 58 receives and stores data, in a similar fashion, from all the probes 30 in all the arrays in the pig 10.

The values of the stresses in the directions of the principal stress axes can then be determined from the resultant experimental measurements of DEP in those directions (i.e. from the first and second probes 30), and from the difference between the values of the SMA signals in the bisecting directions (i.e. from the third and fourth probes 30, which are in the directions in which the SMA signals would be expected to have their minimum and maximum values). This may be done from theoretical analysis, or alternatively by a calibration approach, taking measurements in the manner described above on a sample of material of the same type as that of the pipe 12, while subjecting it to a variety of different stresses. This may be done with a cross-shaped sample, whose arms are aligned with the axes of a test rig, SMA and DEP measurements being made at the centre of the sample where the principal stress directions are aligned with the axes of the test rig. Thus, as described in GB 2 278 450, calibration measurements of DEP from the first probe 30 (i.e. magnetic field parallel to one axis) may be plotted as contours in the stress plane; experimental measurements of DEP from the second probe 30 (i.e. magnetic field parallel to the orthogonal axis) may also be plotted as contours in the stress plane. And the difference between the quadrature SMA measurements from the third and fourth probes 30 may also be plotted as contours in the stress plane. These calibration maps can then be used to determine the biaxial stress in the pipe wall from the measurements of these parameters as the pig 10 moves through the pipe 12. In practice it may be easier to perform these calibrations using a single probe, similar to but smaller than one of the probes 30.

It will be appreciated that the array of probes 30 obtains DEP measurements from all four probes 30, not just the probes 30 aligned with the principal stress axes; the measurements of DEP from the other probes may be used to obtain more accurate determinations of the values parallel to the principal stress axes, because the variation of DEP signal with angle should follow a cosine graph.

It will be appreciated that an inspection pig of the invention may differ from that described above. For example the array may be supported by a different resilient support. Indeed the probes 30 within an array might be supported separately. The number of arrays used to inspect pipe might be 2, 3 or 5, for example, and there may be a different number of probes 30 within an array, for example 2, 3, 5 or 6. The sensors for the SMA and DEP signals may differ from those described, for example the SMA signal might be sensed by a Hall effect sensor or a magneto-resistor; the DEP signal might instead be determined by monitoring the impedance of the drive coil 36, so that no sensing coil 36 would be required. A linear array of the probes 30 may also be used to inspect flat objects rather than pipes, for example being scanned along a rail or girder or steel plate, and the relative motion may arise from movement of the object rather than of the array. Similarly, linear arrays of probes 30 may be used to inspect a drilling pipe from the outside, to measure stresses in the pipe wall. Such an array may be moved manually, or by a vehicle, rather than a pig.

What is claimed is:

1. An apparatus for measuring stress in an object of ferromagnetic material, the apparatus comprising a linear array of probes, and a support structure for the array that is arranged to move relative to the object so that the probes in the array pass in succession over a location on the surface of the object; each probe comprising an electromagnet means defining an electromagnetic core and two spaced apart electromagnetic poles, and means to supply an alternating electric current to generate an alternating magnetic field in the electromagnet means and consequently in the object, and a magnetic sensor arranged to sense the reluctance of that part of the magnetic circuit between the poles of the electromagnet means and to generate a corresponding signal that can be resolved into components in phase with the alternating current and in quadrature to it; wherein the frequency of the alternating magnetic field, the width of each probe, and the velocity of the array relative to the object are such that the said frequency is significantly greater than that calculated by dividing the said velocity by twice the said width; and wherein successive probes in the array are oriented differently so that the corresponding orientations of the magnetic field in the object are different.

2. An apparatus as claimed in claim 1 wherein the array comprises a linear array of probes wherein at least a plurality of the probes include a first magnetic sensor between the two poles and arranged to sense magnetic flux density perpendicular to the direction of the free space magnetic field between the poles, and at least a plurality of the probes include a second magnetic sensor arranged to sense the reluctance of that part of the magnetic circuit between the poles of the electromagnet means.

3. An apparatus as claimed in claim 1 wherein the face of each probe is of width and breadth at least 50 mm, but no larger than 350 mm.

4. An apparatus as claimed in claim 1 wherein the face of each probe is of width and breadth at least 100 mm.

5. An apparatus as claimed in claim 1 also comprising means to process the signals representing the reluctance of the said part of the magnetic circuit into components thereof in phase with the alternating current and in quadrature to it.

6. An apparatus as claimed in claim 1 wherein the array comprises less than ten probes.

7. An apparatus as claimed in claim 6 wherein the array comprises probes oriented at 0°, 45°, 90° and 135° relative to the direction of motion.

8. A method of measuring stress in an object of ferromagnetic material by using an apparatus as claimed in claim 1.

* * * * *